US008142708B2

(12) United States Patent
Schwartz et al.

(10) Patent No.: US 8,142,708 B2
(45) Date of Patent: Mar. 27, 2012

(54) MICRO FLUIDIC SYSTEM FOR SINGLE MOLECULE IMAGING

(75) Inventors: David C. Schwartz, Madison, WI (US); Eileen T. Dimalanta, Madison, WI (US); Juan J. de Pablo, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 2306 days.

(21) Appl. No.: 10/713,898

(22) Filed: Oct. 18, 2002

(65) Prior Publication Data
US 2006/0088944 A1 Apr. 27, 2006

Related U.S. Application Data

(63) Continuation-in-part of application No. 09/962,802, filed on Sep. 24, 2001, now Pat. No. 6,610,256, which is a continuation of application No. 08/855,410, filed on May 13, 1997, now Pat. No. 6,294,136, which is a continuation of application No. 08/415,710, filed on Apr. 3, 1995, now Pat. No. 5,720,928.

(60) Provisional application No. 60/419,884, filed on Oct. 18, 2002.

(51) Int. Cl.
G01N 1/10 (2006.01)
(52) U.S. Cl. .......................... 264/435; 436/174; 435/6.1
(58) Field of Classification Search .................. None
See application file for complete search history.

(56) References Cited

U.S. PATENT DOCUMENTS

| | | | |
|---|---|---|---|
| 4,473,452 A | 9/1984 | Cantor et al. | |
| 4,695,548 A | 9/1987 | Cantor et al. | |
| 4,737,251 A | 4/1988 | Carle et al. | |
| 4,767,700 A | 8/1988 | Wallace | |
| 4,870,004 A | 9/1989 | Conroy et al. | |
| 5,059,294 A | 10/1991 | Lizardi | |
| 5,079,169 A | 1/1992 | Chu et al. | |
| 5,314,829 A | 5/1994 | Coles | 436/165 |
| 5,356,776 A * | 10/1994 | Kambara et al. | 435/6 |
| 5,380,833 A | 1/1995 | Urdea | |
| 5,720,928 A | 2/1998 | Schwartz | 422/186 |
| 5,985,549 A | 11/1999 | Singer et al. | 435/6 |
| 6,054,034 A | 4/2000 | Soane et al. | |
| 6,123,819 A | 9/2000 | Peeters | |
| 6,265,153 B1 * | 7/2001 | Bensimon et al. | 435/6 |
| 6,438,279 B1 | 8/2002 | Craighead et al. | |
| 6,509,158 B1 * | 1/2003 | Schwartz | 435/6 |
| 6,610,256 B2 | 8/2003 | Schwartz | |
| 6,696,022 B1 * | 2/2004 | Chan et al. | 422/99 |
| 6,766,817 B2 | 7/2004 | Silva | |
| 7,049,074 B2 * | 5/2006 | Schwartz | 435/6 |
| 2002/0037499 A1 | 3/2002 | Quake et al. | |
| 2002/0081744 A1 | 6/2002 | Chan et al. | |
| 2002/0137218 A1 | 9/2002 | Mian et al. | |
| 2003/0165964 A1 | 9/2003 | Hannah | |

FOREIGN PATENT DOCUMENTS

| | | |
|---|---|---|
| FR | 2605472 | 4/1988 |
| WO | WO 84/02001 | 5/1984 |
| WO | WO 87/01955 | 9/1987 |
| WO | WO 94/18218 | 8/1994 |
| WO | WO 00/09757 | 2/2000 |

OTHER PUBLICATIONS

Kaiser et al. "Spermine Protection of coliphage lambda deoxyribonucleic acid (DNA) against breakage by hydrodynamic shear", Journal of Molecular Biology, 1963, vol. 6, p. 141-7.*
Miyachi et al. (Journal of Clinical Microbiology, 2000, vol. 38, No. 3, p. 18-21).*
Shrewsbury et al. (International Conference on Modeling and simulation of Microsystems, Semiconductors, Sensors and Actuators, San Juan Puerto Rico, Apr. 19-22, 1999, p. 578-580; IDS reference).*
Perkins et al. (Science, 1995, 268(5207):83-87).*
Kiba et al., "DNA analysis by microfabricated capillary electrophoresis device," Nucleic Acids Symp. Ser., 1999, 42:57-58.
Shrewsbury P et al., "Characterization of DNA flow through microchannels," International conference on Modeling and Simulation of Microsystems, Semiconductors, Sensors and Actuators, San Jan, Puerto Rico, Apr. 19-22, 1999, pp. 578-580.
Zhao B et al., "Surface-directed liquid flow inside microchannels," Science, 2001, 291:1023-1026.
PCT Int'l Search Report.
Chih-Ming Ho, "Fluidics—The Link Between Micro and Nano Sciences and Technologies", Proceedings of the IEEE 14th Annual International Conference on Microelectro Mechancial Systems. MEMS 2001. Interlaken, Switzerland, Jan. 21-25, 2001, IEEE International Micro Electro Mechanical Systems Conference, New York, NY: IEEE, US, vol. CONF. 14, (Jan. 21, 2001), pp. 375-384, XP010534628 ISBN: 0-7803-5998-4, p. 378-379.
Unger M A Et Al: "Monolithic Microfabricated Valves and Pumps by Multilayer Soft Lithography", Science, American Association for the Advancement of Science, US, vol. 288, Apr. 7, 2000, pp. 113-116, XP002192277 ISSN: 0036-8075 Figure 1.
Stix, Gary; "Thinking Big-A Harvard Medical School dropout aims to usher in the personal-genomics ear," Innovations, Scientific American, Jun. 2002, pp. 30-31.
Stikeman, Alexandra, "Nanobiotech Makes the Diagnosis," Technology Review, May 2002, pp. 61-66.
Chattoraj et al., "DNA Condensation with Polyamines", J. Mol. Biol. 121, (1978), pp. 327-337.
Ohi et al., "Mapping of MItochondrial 4S RNA Genes . . . by Electron Microscopy", J. Mol. Biol. 212, (1978), pp. 299-310.
Manuelidis et al, Biol. Abstr. 76(4); Ref. No. 27153; p. 2940.
Bensimon, A. et al., 1994, "Alignment and Sensitive Detection of DNA by a Moving Interface" Science 265: 2096.
Perkins, T.T. et al., 1994, "Direct Observation of Tube-like Motion of a Single Polymer Chain", 264: 819-822.

(Continued)

*Primary Examiner* — Stephanie K Mummert
(74) *Attorney, Agent, or Firm* — Quarles & Brady LLP

(57) ABSTRACT

Laminar flow of a carrier liquid and polymeric molecules through micro-channels is used to straighten the polymeric molecules and attach the straightened molecules to a wall of the micro-channel for subsequent treatment and analysis. Micro-channels can be manufactured using an elastic molding material. One micro-channel embodiment provides fluid flow using a standard laboratory centrifuge.

5 Claims, 2 Drawing Sheets

OTHER PUBLICATIONS

Cohen et al., 1993, "A first-generation physical map of the human genome", Nature 366: 698-701.
Guo et al., 1993, "Sizing of Large DNA Molecules by Hook Formation in a Loose Matrix", J. Biomol. Structure and Dynamics 11: 1-10.
Hansma, H.G. et al., 1993, "Atomic force microscopy of DNA in aqueous solutions", Nucleic Acids Research 21: 505-512.
Karrasch, S. et al., 1993, "Covalent Binding of Biological Samples to Solid Supports for Scanning Probe Microscopy in Buffer Solution" Biophysical J. 65: 2437-2446.
Koob et al., 1992, "RecA-AC: single-site cleavage of plasmids and chromosomes at any predetermined restriction site" Nucleic Acids Res. 20:5831.
Zenhausern et al., 1992, "Imaging of DNA by Scanning Force Microscopy", J. Struct. Biol. 108: 69-73.
Lyubchenko et al., 1992, "Atomic Force Microscopy Imaging of Dougle Stranded DNA and RNA", J. Biomol. Struct. and Dyn. 10: 589-606.
Bustamante et al., 1992, "Circular DNA Molecules Imaged in Air by Scanning Force Microscopy", Biochemistry 31: 22-26.
van denEngh, et al., 1992, "Estimating Genomic Distance from DNA Sequence Location in Cell Nuclei by a Random Walk Model", Science 257: 1410.
Allison et al., 1992, "Immobilization of DNA for scanning probe microscopy", Proc. Natl. Acad. Sci. USA 89: 10129-10133.
Heng et al., 1992, "High-resolution mapping of mammalian genes by in situ hybridization to free chromatin", Proc. Natl. Acad. Sci. USA 89: 9509.
Maier et al., 1992, "Complete coverage of the *Schizosaccharomyces pombe* genome in yeast artificial chromosomes", Nat. Genet. 1:273.
Guo et al., 1992, "Sizing single DNA molecules", Nature 359:783-784.
Chumakov et al., 1992, "Continuum of overlapping clones spanning the entire human chromosome 21q", Nature 359:380.
Link, 1991, "Physical Map of the *Saccharomyces cerevisiae* Genome at 110-Kilobase Resolution", Genetics 127: 681.
Ferrin et al., 1991, "Selective Cleavage of Human DNA: RecA-Assisted Restriction Endonuclease (RARE) Cleavage", Science 254: 1494.
Campbell et al., 1991, "Generation of a nested series of interstitial deletions in yeast artificial chromosomes carrying human DNA", Proc. Natl. Acad. Sci. USA 88:5744.
Cavalli-Sforza, 1990, "Opinion: How Can One Study Individual Variation for 3 Billion Nucleotides of the Human Genome", Am. J. Hum. Genet. 46: 649.
Koob et al., 1990, "Cleaving Yeast and *Escherichia coli* Genomes at a single site", Science 250: 271-273.
Lichter et al., 1990, "High-Resolution Mapping of Human Chromosome 11 by in Situ Hybridization with Cosmid Clones" Science 247: 64.
Stallings et al., 1990, "Physical mapping of human chromosomes by repetitive sequence fingerprinting", Proc. Natl. Acad. Sci. USA 87: 6218-6222.
Glazer et al., 1990, "A stable double-stranded DNA-ethidium homodimer complex: Application to picogram fluorescence detection of DNA in agarose gels", Proc. Natl. Acad. Sci. USA 87: 3851.
Schwartz et al., 1989, "ED: pulsed electrophoresis instrument", Nature 342: 575-576.
Lawrence et al., 1988, "Sensitive, High-Resolution Chromatin and Chromosome Mapping In Situ: Presence and Orientation of Two Closely Integrated Copies of EBV in a Lymphoma Line", Cell 52:51.
Barlow et al., 1987, Genetics by gel electrophoresis: the impact of pulsed field gel electrophoresis on mammalian genetics:, Trends in Genetics (3): 167-177.
Burke et al., 1987, "Cloning of Large Segments of Exogenous DNA into Yeast by Means of Artificial Chromosome Vectors", Science 236: 806.
Church and Gilbert, 1984, "Genomic sequencing", Proc. Natl. Acad. Sci. USA 81: 1991.
Luckham and Klein, 1984, "Forces between Mica Surfaces Bearing adsorbed Polyelectrolyte, Poly-L-Iysine, in Aqueous Media", Chem. Soc. Faraday Trans. I, 80: 865-878.

Schwartz and Cantor, 1984, "Separation of Yeast Chromosome-Sized DNAs by Pulsed Field Gradient Gel Electrophoresis", Cell 37: 67.
Murray and Szostak, 1983, "Construction of Artificial Chromosome in Yeast", Nature 305: 189-193.
Manuelidis et al., 1982, "High-resolution Mapping of Satellite DNA using Biotin-labeled DNA Probes", J. Cell Biol. 95: 619.
Matsumoto, et al., 1981, "Light Microscopic Structure of DNA in Solution Studied by the 4',6-Diamidino-2-phenylindole Staining Method", J. Mol. Biol. 132: 501-516.
Gosule and Schellman, 1978, "DNA Condensation with Polyamines", J. Mol. Biol. 121: 311-326.
Porath and Axen, 1976, "Immobilization of Enzymes to Agar, Agarose, and Sephadex Support", Methods Enzymol. 44:19.
Smith and Bimstiel, 1976, "A simple method for DNA restriction site mapping", Nucleic Acids Res. 3: 2387-2399.
Massa et al., 1973, "Flow Properties of High-Molecular-Weight DNA Solutions: Viscosity, Recoil, and:Longest Retardation Time", Biopolymers 12:.
Schwartz et al., 1989, "Conformational Dynamics of Individual DNA Molecules During Gel Electrophoresis", Nature 338:520.
Rampino and Chrambach, 1991, "Conformational correlatives of DNA band compression and bidirectional migration during field inversion gel electrophoresis, detected by quantitative video epifluoresence microscopy", Biopolymers 31: 1297-1307.
Romling et al., 1989, "A physical genome map of *Pseudomonas aeruginosa*", EMBO J. 8(13): 4081-4089.
Smith et al., 1989, "Observation of Individual DNA Molecules Undergoing Gel Electrophoresis", Science 242: 203.
Kucherlapati et al., 1988, Genetic Recombination pp. 92-106.
Zubay, 1988, Biochemistry (Macmillan Publishing Company, New York) pp. 918-919.
Woolf et al., 1988, "Mapping genomic organizatiaon by field inversion and two dimensional gel electrophoresis", Nucleic Acids Research 16(9): 3863.
Carle et al., Electrophoretic Separations of Large DNA Molecules by Periodic Inversion of the Electrif Field, Science 232: 65-68.
Poddar and Maniloff, 1986, "Chromosome analysis by two-dimensional fingerprinting", Gene 49: 93-102.
Stellwagen, N.C., 1985, "Orientation of DNA molecules in agarose gels by pulsed electric fields", J. Biomol. Str. and Dyn. 3(2): 299.
Yanagida et al., 1983, "Dynamic behaviors of DNA Molecules in solution . . . " Cold Spring Harbor Symp. Quant. Biol. 47: 177.
Dev. et al., 1982, "Techniques for chromosome analysis", Techniques in Somatic Cell Genetics, edited by Shay, pp. 493-503.
Manuelidis et al., 1992, "High-resolution mapping of satellite DNA using biotin-labeled DNA probes", Biol. Abstr. 76(4), Ref. No. 27153, p. 2940.
Chattoraj et al., 1978, "DNA Coordination with polyamines", J. Mol. Biol. 121: 327.
Ohi et al., 1978, "Mapping of Mitochondria 4S RNA genes in *Xenopus laevis* by electron microscopy", J. Mol. Biol. 121: 299.
Gurrieri et al., 1990, "Imaging of kinked configurations of DNA molecules undergoing orthogonal field alternating gel electrophoresis by fluorescence microscopy", Biochemistry 29: 3396-3401.
Bendich and Smith, 1990, "Moving pictures and pulsed-field gel electrophoresis show linear DNA molecules form chloroplasts and mitochondria" Current Genetics 17: 421-425.
Smith and Bendich, 1990, "Electrophoretic charge density and persistance length of DNA as measured by fluorescence microscopy", Biopolymers 29(8-9): 1167.
Sturm and Weill, 1989, "Direct observation of DNA chain orientation and relaxation by electric birefringence: Implications for the mechanism of separation during pulsed-field gel electrophoresis", Physical Rev. Letters 62(13): 1484.
Stellwagen, 1988, "Effect of pulsed and reversing electric fields on the orientation of linear and supercoiled DNA molecules in Agarose Gels", Biochemistry 27: 6417.
Schwartz, et al., "Conformational Dynamics of Individual DNA Molecules During Gel Electrophoesis", Nature, Apr. 6, 1989, pp. 520-522.
Poddar et al., Chromosome analysis by two-dimensional fingerprinting, Gene, 49 (1986), pp. 93-102.

Woolf et al., "Mapping genomic organization by field inversion and two dimensional gel electrophoresis", Nucleic Acid Research, vol. 16, No. 9 (1988), pp. 3863-3875.

Roemling et al., "A physical genome map of *Pseudomonas aeruginosa*", The EMBO Journal, vol. 8, No. 13 (1989), pp. 4081-4089.

Yanagida et al., "Dynamic Behaviors of DNA Molecules in Solution . . . ", Cold Sprg. Hrbr. Symp. Quant. Biol. 47, pp. 177-187, 1983.

Zubay, Biochemistry, 1988, pp. 918-919.

Kucherlapati et al., Genetic Recombination, 1988, pp. 92-106.

Smith et al., "Observation of Individual DNA Molecules Undergoing Gel Electrophoresis", Science 242, Jan. 13, 1989 pp. 203-206.

Carle et al., "Electrophoretic Separations of Large DNA molecules . . . ", Science, Apr. 4, 1986, pp. 65-68.

Dev. et al., "Techniques for Chromosome Analysis", Techniques in SOmatic Cell Genetics, edited by Shay, 1982, pp. 493-503.

Rampino, "The Physics of Gel Electrophoresis".

Stellwagon, "Effect of Pulsed and Reversing Electric Fields . . . " Biochem. 17, 1988, pp. 6417-6424.

Manuelidis et al., Biol. Abstr. 76(4), Ref. No. 27153, p. 2940.

Gerlach et al. (1984) Cytometry 5:562-571.

K. R. Khrapko et al., "A Method for DNA Sequencing by Hybridization With Oligonucleotide Matrix", J. DNA Sequencing and Mapping, 1991, vol. 1, pp. 375-388.

R. C.Williams, "Use of POlylysine for Adsorption of Nucleic Acids and Enzymes to Electron Microscope Specimen Films", Proc. Natl. Acad. Sci. USA, vol. 74, No. 6, pp. 2311-2315, Jun. 1977.

F. Fish et al., "A sensitive Solid Phase Microradioimmunoassay for Anti-Dougle Stranded DNA Antibodies", Arthritis and Rheumatism, vol. 24, No. 3 (Mar. 1981).

Barlow and Lehrach, 1987, "Genetics by Gel Electrophoresis: The Impact of Pulsed Field Gel Electrophoresis on Mammalian Genetics", Trends in Genetics 3: 167-171.

Bensimon, et al., 1994, "Alignment and Sensitive Detection of DNA by a Moving Interface" Science 265: 2096-2098.

Carle et al., 1986, "Electrophoretic Separations of Large DNA Molecules by Periodic Inversion of the Electric Field", Science 232: 65-68.

Dev et al., 1982, "Techniques for Chromosome Analysis", Techniques in Somatic Cell Genetics, edited by Shay, pp. 493-503.

Ferrin and Camerini-Otero, 1991, "Selective Cleavage of Human DNA: RecA-Assisted Restriction Endonuclease (RARE) Cleavage", Science 254: 1494-1497.

Fish and Ziff, 1981, "A Sensitive Solid Phase Microradioimmunoassay for Anti-Double Stranded DNA Antibodies", Arthritis and Rheumatism 24: 534-543.

Gerlach et al., 1984, "Application of a High-Resolution TV-Microscope System to Estimate the Sequence of Centromere Separation in Muntjak Chromosomes", Cytometery 5: 562-571.

Gosule and Schellman, 1978, "DNA Condensation with Polyamines I. Spectroscopic Studies", J. Mol. Biol. 121: 311-326.

Guo et al., 1992, "Sizing Single DNA Molecules", Nature 359: 783-784.

Hansma et al., 1993, "Atomic Force Microscopy of DNA in Aqueous Solutions", Nucl. Acid Res. 21: 505-512.

Karrasch, et al., 1993, "Covalent Binding of Biological Samples to Solid Supports for Scanning Probe Microscopy in Buffer Solution", Biophysical J. 65: 2437-2446.

Koob and Szybalski, 1990, "Cleaving Yeast and *Escherichia coli* Genomes at a Single Site", Science 250: 271-273.

Khrapko et al., 1991, "A Method for DNA Sequencing by Hybridization with Oligonucleotide Matrix", J. DNA Sequencing and Mapping, 1: 375-388.

Kucherlapati et al., 1988, Genetic Recombination p. 92-106.

Lawrence et al., Mapping In Situ: Presence and Orientation of Two Closely Integrated Copies of EBV in a Lymphoma Line, Cell 52: 51-61, 1988.

Link and Olson, 1991, "Physical Map of the *Saccharomyces cerevisiae* Genome at 110-Kilobase Resolution", Genetics 127: 681-698.

Lodish et al., 1995, Molecular Cell Biology, W.H. Freeman, NY, p. 345.

Lyubchenko et al., 1992, "Atomic Force Microscopy Imaging of Double Stranded DNA and RNA", J. Biomol. Struct. and Dynam. 10: 589-606.

Massa, 1973, "Flow Properties of High-Molecular-Weight DNA Solutions: Viscosity, Recoil, and Longest Retardation Time", Biopolymers 12: 1071-1081.

Matsumoto et al., 1981, "Light Microscopic Structure of DNA in Solution Studied by the 4',6-Diamidino-2-phenylindole Staining Method", J. Mol. Biol. 152: 501-516.

Murray and Szostak, 1983, "Construction of Artificial Chromosomes in Yeast", Nature 305: 189-193.

Perkins et al., 1994, "Direct Observation of Tube-like Motion of a Single Polymer Chain", Science 264: 819-822.

Schwartz et al., 1984, "Separation of Yeast Chromosome-Sized DNAs by Pulsed field Gradient Gel Electrophoresis", Cell 37: 67-75.

Smith et al., 1992, "Direct Mechanical Measurements of the Elasticity of Single DNA Molecules by Using Magnetic Beads", Science 258: 1122-1126.

Smith and Bendich, 1990, "Electrophoretic Charge Density and Persistence Length of DNA as Measured by Fluorescence Microscopy", Biopolymers 29: 1167-1173.

Southern, 1975, "Detection of Specific Sequences among DNA Fragments Separated by Gel Electrophoresis", J. Mol. Biol. 98: 503-517.

van den Engh et al., 1992, "Estimating Genomic Distance from DNA Sequence Location in Cell Nuclei by a Random Walk Model", Science 257: 1410-1412.

Williams, 1977, "Use of Polylisine for Adsorbtion of Nucleic Acids and Enzymes to Electron Microscope Specimen Films", Proc. Natl. Acad. Sci. USA 74: 2311-2315.

Woolf et al., 1988, "Mapping Genomic Organization by Field Inversion and Two Dimensional Gel Electrophoresis", Nucl. Acids Res. 16: 3863-3875.

Houseal et al., 1989, "Real-Time Imaging of Single DNA Molecules with Fluorescence Microscopy", Biophys. J. 56: 507-516.

* cited by examiner

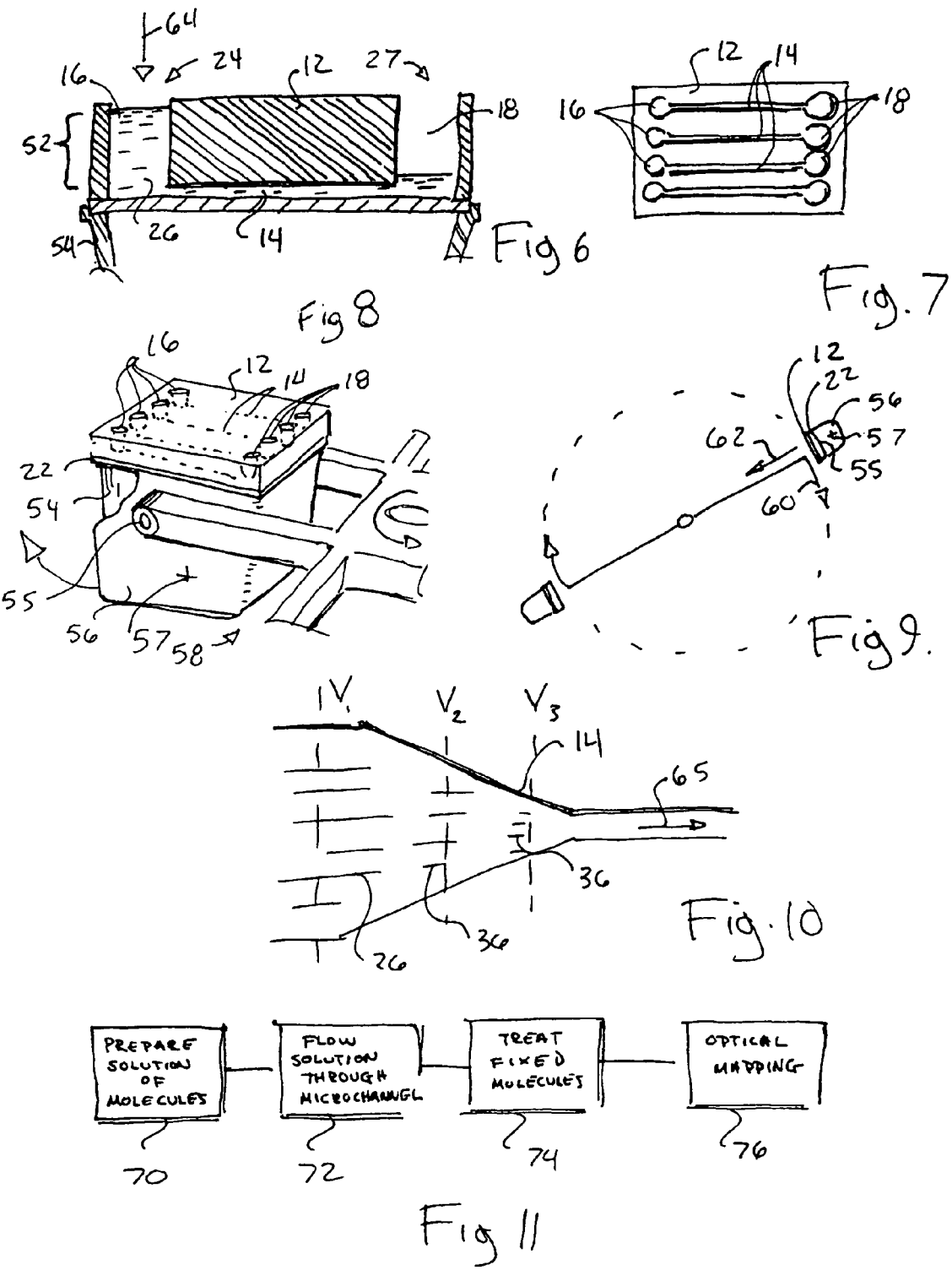

MICRO FLUIDIC SYSTEM FOR SINGLE MOLECULE IMAGING

CROSS-REFERENCE TO RELATED APPLICATIONS

This application, which has been converted into a nonprovisional patent application from U.S. provisional patent application No. 60/419,884 filed Oct. 18, 2002, is a continuation-in-part of U.S. patent application Ser. No. 09/962,802 filed Sep. 24, 2001, now U.S. Pat. No. 6,610,256, which is a continuation of U.S. patent application Ser. No. 08/855,410 filed May 13, 1997, now U.S. Pat. No. 6,294,136, which is a continuation of U.S. patent application Ser. No. 08/415,710 filed Apr. 3, 1995, now U.S. Pat. No. 5,720,928.

STATEMENT REGARDING FEDERALLY SPONSORED RESEARCH OR DEVELOPMENT

This invention was made with United States government support awarded by the following agencies: DOE DE-FGO2-99ER62830 and NIH HG00225.
The United States has certain rights in this invention.

BACKGROUND OF THE INVENTION

The present invention relates to methods of manipulating molecules and, in particular, to a fluid transport system useful for straightening, aligning, and fixing long chain polymers such as DNA.

The analysis of nucleic acid molecules (e.g. DNA) and, in particular, the sequencing of such molecules may be aided by optical techniques in which long portions of such molecules are straightened and fixed to a substrate for microscopic analysis. The fixed molecule may be analyzed by creating "landmarks" on the molecule by attaching fluorescent markers to specific locations or by cutting it with restriction enzymes to form visible breaks at specific locations. The order and relative separation of the landmarks is preserved, because the molecule remains fixed, and may be used to produce an optical map of the molecule. The optical map provides a framework on which other sequence information may be assembled. The landmarks allow optical maps of fragments of long molecules to be assembled into the entire molecule by the process of matching fragments with similarly spaced landmarks.

The effective use of optical maps requires that large numbers of single molecules be processed. A number of techniques have been examined for the purpose of straightening and fixing large numbers of molecules including: (1) straightening the molecules in a flow of molten gel which is then hardened to fix the molecules in place and (2) straightening the molecules under capillary flow of a carrier liquid or convective flow caused by evaporation of a carrier liquid and promoting adsorption of the elongated molecules to a substrate adjacent to the flow.

A different set of techniques has been investigated in which the molecules are straightened in a flowing carrier fluid without being fixed to a substrate. In these techniques, the molecules are analyzed as they move. While these latter techniques potentially provide the same benefits of preserving the order and relative separation of the landmarks, motion of the molecule complicates the process of imaging the molecule, makes some landmarking techniques difficult, and eliminates the possibility of preserving the molecule for later additional or more complex analysis.

Ideally, when molecules are fixed to a substrate, the fixed molecules should have sufficient separation so that molecules do not overlap or cross. Points of overlap create image artifacts that can severely hamper the analysis process.

It is typical to stain the fixed molecule with a fluorescent material which distributes itself evenly along the molecule allowing estimates of separation between landmarks (e.g., in numbers of base pairs) to be gauged by total fluorescence rather than strictly by length. Such fluorescence measurements work best if the elongation of the molecule during straightening is not so great as to decrease the fluorescence per length of the molecule to a background level. Inadequate elongation of the molecule, however, can make it difficult to identify the points cut by the restriction enzymes, which desirably separate slightly under relaxation of the elongated molecule to render the cuts visible.

Prior art techniques for elongating and fixing long chain molecules can produce excessive overlap among molecules and variation in molecule elongation.

SUMMARY OF THE INVENTION

The present invention provides a method for straightening and fixing polymeric molecules using well-controlled laminar flow in a micro-channel. The laminar flow within a micro-channel allows sufficient diffusion of the ends of the molecule so that they may attach themselves to the wall of the micro-channel to be adsorbed and fixed in their straightened configuration.

The present invention also provides an improved apparatus of fabricating micro-channels suitable for this technique using an elastic molding compound.

Additional embodiments of the present invention provide the ability to sort molecular fragments by length and simple mechanisms for producing the necessary controlled laminar flow.

Specifically, then, the present invention fixes and straightens polymeric molecules using a channel sized to provide laminar flow of a liquid along a channel length, the channel having at least a first wall providing electrostatic attraction to the polymeric molecule. A means is provided for passing the liquid and polymeric molecule through the channel to straighten the polymeric molecule by passage along the channel within the laminar flow and allow absorption of the polymeric molecule to the first wall of the channel in straightened form.

It is thus one object of the invention to provide an improved method of straightening and fixing polymeric molecules. The laminar flow may be controlled to provide more consistent elongation to the molecules and improved separation of the molecules with reduced overlap and better alignment.

The first wall of the channel may be transparent and, for example, constructed of glass.

It is thus another object of the invention to provide an optical mapping surface well suited for use with optical microscopes.

The first wall may be treated to have a positive surface charge of predetermined density.

Thus, it is another object of the invention to control the electrostatic attraction between the polymeric molecule and the optical mapping substrate for more precise control over the fixing process.

The first wall may be detachable from the channel.

It is another object of the invention to provide an optical mapping surface having improved accessibility and/or reusability.

The channel may have at least one end that provides a funnel section opening to a reservoir holding the liquid and polymeric molecules.

It is thus another object of the invention to provide a simple means for staging the polymeric molecules and one that allows introduction of the polymeric molecules into the channel with minimum breakage.

The means for passing the liquid and polymeric molecules through the channel may, for example, be a pressure pump attached to one end of the channel, for example, a syringe or other type of pump, or a negative pressure pump attached to the other end of the channel such as may draw the liquid through by pressure differential, also, for example, being a syringe or other type of pump. Alternatively, the means may be a reservoir acted on by a force resulting from centrifugal acceleration of the channel and reservoirs.

Thus, it is another object of the invention to provide a variety of means of producing the necessary controlled laminar flow in the channel.

The reservoir used when centrifugal acceleration provides the movement of the liquid may be an end well extending perpendicularly to the length of the channel and the apparatus may further include a housing allowing the end well and channel to be received by a centrifuge with the end well extending along a principal axis of centrifugal acceleration, and the channel extending substantially across the principal axis of centrifugal acceleration.

Thus, it is another object of the invention to provide a simple apparatus that makes use of a standard laboratory centrifuge to produce the necessary flows and which thus may be inexpensive and/or disposable.

The apparatus may include multiple end wells and multiple micro-channels.

Thus, it is another object of the invention to allow simultaneous parallel straightening and fixation of the same or different polymeric molecules to occur to increase the throughput of the analysis process.

The channel may include a region of varying cross-section to promote a gradient in the laminar flow rate.

Thus, it is another object of the invention to provide for a sorting of molecules by length, taking advantage of differences in diffusion rate of the ends of the molecule as a function of molecular length.

These particular objects and advantages may apply to only some embodiments falling within the claims and thus do not define the scope of the invention.

BRIEF DESCRIPTION OF THE DRAWINGS

FIG. 6 is an elevational, cross-sectional view of an alternative embodiment of the present invention in which centrifugal acceleration acting on a fluid head in the staging reservoir causes laminar flow in the micro-channel;

FIG. 7 is a plan view of the embodiment of FIG. 6 showing multiple parallel micro-channels each with staging wells and receiving wells;

FIG. 8 is a perspective view of the embodiments of FIGS. 6 and 7 as placed in a standard centrifuge cup, the latter in partial cut-away;

FIG. 9 is a simplified diagram of rotation of centrifuge cup of FIG. 8 showing the vectors of motion and centripetal acceleration;

FIG. 10 is a plan view of an alternative micro-channel design providing varying cross-sections and inversely varying flow velocity such as may be used to sort polymeric molecules by size along the length of the micro-channel; and FIG. 11 is a flow diagram of the process of using the present invention to straighten and fix polymeric molecules.

DETAILED DESCRIPTION OF THE PREFERRED EMBODIMENT

Figure 1:
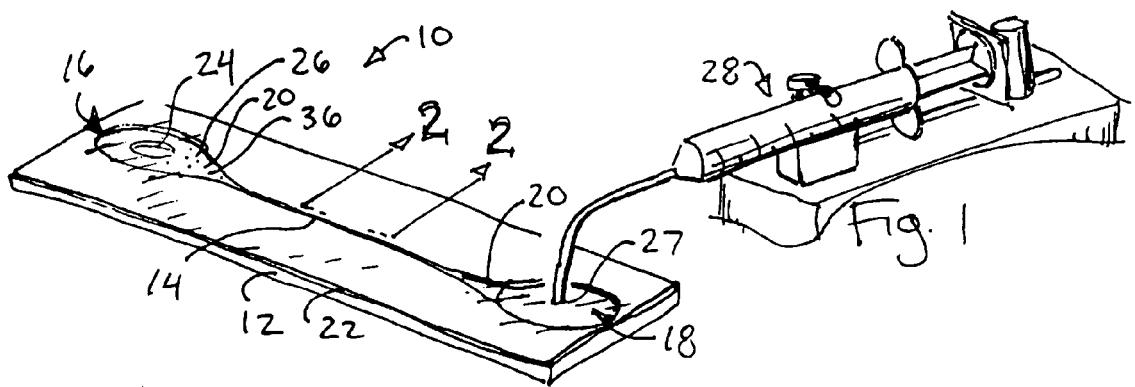
FIG. 1 is a perspective view of one embodiment of the present invention showing a micro-channel communicating between a staging reservoir, holding polymeric molecules in a carrier liquid, and a collecting reservoir, the micro-channel attached to the reservoirs by funnel portions reducing shear and promoting laminar flow in the micro-channel and showing the use of a syringe pump to draw liquid through the micro-channel.

Referring now to FIG. 1, the apparatus 10 of the present invention provides a generally planar channel plate 12 into which a longitudinally extending micro-channel 14 is formed, flanked by a staging reservoir 16 and a collecting reservoir 18 positioned at longitudinal ends of the channel plate 12.

Junctions between the longitudinal ends of the micro-channel 14 and staging reservoir 16 and collecting reservoir 18 are tapered to create funnel sections with narrow ends attached to the micro-channel 14 and wide ends attached to one of the staging reservoir 16 or collecting reservoir 18. The funnel sections 20 provide a smooth transition of fluid from the staging reservoir 16 through the micro-channel 14 to the collecting reservoir 18 thereby promoting laminar flow within the micro-channel 14 and reducing breakage of polymeric molecules as will be described.

One common wall of the staging reservoir 16, the collecting reservoir 18, and the micro-channel 14 is provided by an optical mapping substrate 22 attached to the channel plate 12. The substrate 22 thus encloses the staging reservoir 16, the collecting reservoir 18, and the micro-channel 14. The substrate 22, for example, may be a glass slide, treated as will be described below In the embodiment of FIG. 1, a sample introduction port 24 may be formed in the optical mapping substrate 22 at the staging reservoir 16 to allow the introduction of polymeric molecules 36 and a carrier liquid 26 to the staging reservoir. In particular embodiments, the sample introduction port 24 may be used for pressure equalization when materials are drawn through the micro-channel 14 or for the attachment of a pump to pressurize the staging reservoir 16 to cause materials to flow through the micro-channel 14.

Similarly, a sample extraction port 27 may be formed in the optical mapping substrate 22 at the collecting reservoir 18 for removal of material, pressure equalization, or as shown, the attachment of pump 28 to draw the materials through the micro-channel 14. Alternatively, the ports 24 and 27 may be formed in the channel plate 12

In the embodiment of FIG. 1, the pump 28 is a syringe pump providing precisely metered flow using an electromechanical actuator and control system as is well understood in the art. The syringe pump draws carrier liquid 26 and polymeric molecules 36 from staging reservoir 16 through the micro-channel 14 in the collecting reservoir 18 at a controlled flow rate as may be set to provide the desired laminar flow within the micro-channel 14.

Figure 2:
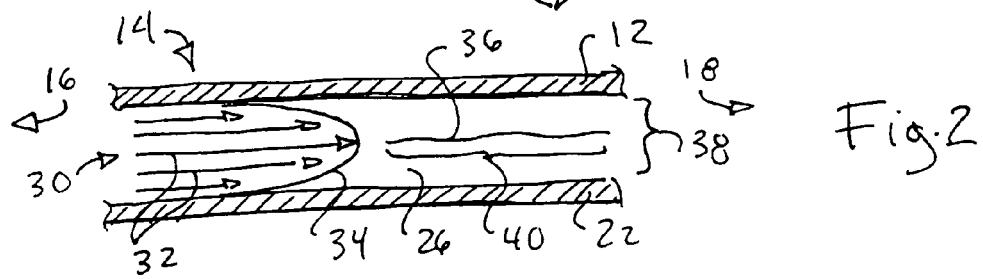
FIG. 2 is a cross-sectional view of the channel along lines 2-2 of FIG. 1 showing the increasing velocity of the laminar flow in the micro-channel toward the center of the micro-channel and an elongated DNA molecule centered in the micro-channel by the laminar flow.

Specifically, referring to FIG. 2, the laminar flow 30 of carrier liquid 26 and polymeric molecules 36 within the micro-channel is such as to provide flow 32 parallel to the longitudinal walls of the micro-channel 14 with greatest flow velocities toward the cross-sectional center of the micro-channel 14 thereby defining a flow velocity profile 34. The flow rate of the pump 28 and the size of the micro-channel 14 is selected to provide flow velocity profile 34 that promotes straightening of the particular polymeric molecule 36 contained within the carrier liquid 26 with the polymeric molecule 36 roughly centered within the lumen of the micro-channel 14. These setting may be determined empirically by visual observation of the polymeric molecules 36 at different flow rates. Generally, laminar flow may be distinguished from capillary flow in which the liquid is drawn along the surface of the micro-channel 14 walls by a hydrophilicity of those walls and where the center leading flow velocity profile 34 is not obtained.

In a 50-micrometer wide micro-channel 14, for example, the velocity of flow 32 may range from 15 to 70 micrometers per second as measured across the lumen of the micro-channel 14.

In one embodiment, the cross-sectional width 38 of the micro-channel 14 is 50 micrometers and is preferably less than 100 micrometers. More generally, it is believed that the width 38 will be between one and one hundred times the straightened length 40 of the polymeric molecule 36.

Figure 3:
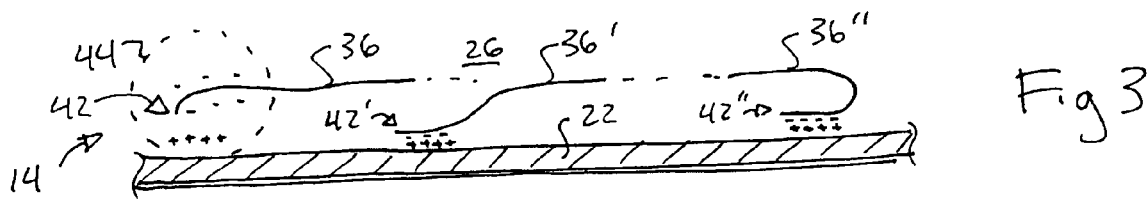
FIG. 3 is a fragmentary view similar to FIG. 2 showing: a diffusion radius of one end of a polymeric molecule prior to adsorption to a wall of the micro-channel; a polymeric molecule having a trailing end attached to the wall of the micro-channel; and a polymeric molecule having a leading end attached to the wall of the micro-channel prior to adsorption of the entire length of the polymeric molecule to the wall of the micro-channel.

Referring now to FIG. 3, although the inventors do not wish to be bound by a particular theory, it is believed that the ends 42 of the polymeric molecule 36 are more mobile than the remainder of the polymeric molecule 36 and may be modeled as having an effective diffusion radius 44 during the time the polymeric molecule 36 is in transit in the micro-channel 14 and generally greater than the polymeric molecule 36 as a whole. The average flow rate of the carrier liquid 26 for the flow velocity profile 34 and the width 38 of the micro-channel 14 is thus adjusted so that this effective diffusion radius 44 is equal to or greater than the width 38 of the micro-channel 14. In this way, at some time during transit of the polymeric molecule 36 within the micro-channel 14, contact by one end 42 of a large number of the polymeric molecules 36 with the substrate 22 can be expected. This contact will cause an electrostatic bond between the substrate 22 and the end 42 of a polymeric molecule 36.

Either the leading or the trailing ends 42 of the polymeric molecule 36 may be the first to attach to the substrate 22. As indicated by polymeric molecule 36', if the trailing end 42' of the polymeric molecule 36" is the first to contact the substrate 22 it is believed that continued flow of the carrier liquid 26 pulls the remainder of the polymeric molecule 36 against the substrate 22 to be held there by electrostatic attraction in a straightened state. Conversely, as indicated by polymeric molecule 36", if the leading end 42" of the polymeric molecule 36" is the first to contact the substrate 22 it is believed that continued flow of the carrier liquid 26 rolls the remainder of the polymeric molecule 36 over and then draws it against the substrate 22 to be held there by electrostatic attraction in a straightened state.

In order to promote and control attachment of the polymeric molecule to the substrate 22, the substrate 22 may be treated to establish a positive charge density on its surface contacting the carrier liquid 26. For example, the surface may be derivative with silage compounds, for example, those discussed in U.S. Pat. No. 5,720,928 hereby incorporated in its entirety by reference.

Whereas the micro-channels 14 and optionally the staging reservoir 16 and collecting reservoir 18 of the apparatus 10 may be constructed in silicon using conventional photolithographic techniques, in a preferred embodiment of the present invention, the micro-channels 14 (and optionally the staging reservoir 16 and collecting reservoir 18) are constructed using a molded elastomeric polymer.

Figure 4:
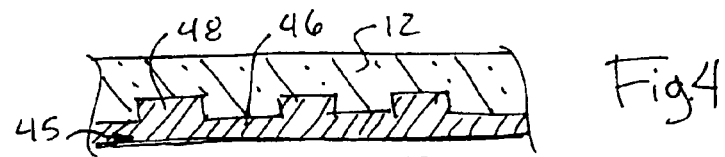
FIG. 4 is a cross-sectional view of multiple micro-channels during a first step of manufacturing the micro-channels in which a mold is used with an elastic molding compound to form upper walls of the micro-channels.

Referring now to FIG. 4, in particular, a mold 45 providing a planar substrate 46 with upstanding ridges 48 defining the volume of the micro-channels 14 may be fabricated using conventional photolithography in which a light sensitive photoresist is applied to a silicon wafer that will form the mold 45. The photoresist is hardened by selective optical exposure and the unhardened portions washed away so that the photoresist provides a mask in the regions of the upstanding ridges 48 (e.g., the regions of the micro-channels 14 and the staging reservoir 16 and collecting reservoir 18). The silicon wafer is then etched to a depth of 7 to 8 micrometers defining the height of the micro-channel 14.

Referring still to FIG. 4, an elastomeric polymer, preferably poly(dimethylsiloxane) "PDMS") is then poured over this mold 45 to create the channel plate 12. The PDMS channel plate 12 is then peeled from the mold 45 and exposed to oxygen plasma to make it hydrophilic.

Figure 5:
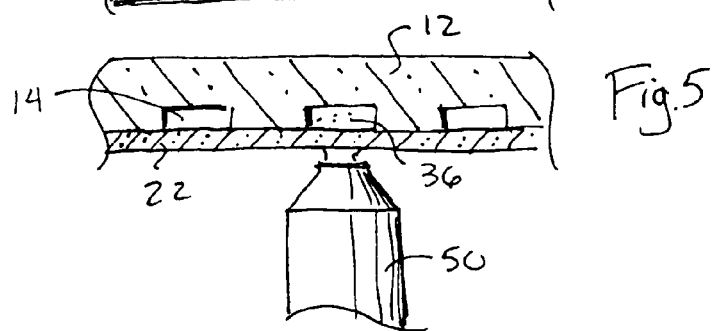
FIG. 5 is a figure similar to FIG. 4 showing removal of the mold and attachment of the upper walls of the micro-channel to a glass optical mapping surface in a second step of manufacturing.

As shown in FIG. 5, the channel plate 12 may then be adhered to the substrate 22 creating the micro-channels 14 and optionally the staging reservoir 16 and collecting reservoir 18. The PDMS of the channel plate 12 will naturally adhere to glass in a releasable manner to produce a leak resistant seal. The seal is strong enough to resist leakage of fluids filling the micro-channels for the pressures used in this process yet weak enough to be reversible, and thus make the channel plate 12 and substrates 22 reusable.

By treatment of the substrate 22, as described above, to impress upon it a positive charge, and lack of treatment of channel plate 12 or by a treatment that promotes a negative surface charge on the channel plate 12 (?) preferential adsorption of the polymeric molecules 36 by the substrate 22 may be promoted. Optical mapping of the fixed polymeric molecules 36 may then be done through the transparent glass substrate 22 by means of an inverted microscope objective 50 such as a Zeiss Axiovert 135M such as is readily commercially available. Before the optical mapping, the polymeric molecule may be treated with fluorescent markers or restriction enzymes as are understood in the art.

Alternatively, because the channel plate 12 is attached to the substrate 22 releasable, the substrate 22 may be removed from the channel plate 12 and the top surface of the substrate 22 may be imaged. The removal of the channel plate 12 may also assist in further treatment of the fixed polymeric molecules 36, for example, with restriction enzymes and the like and the drying of these molecules to further promote adhesion. The ability to separate the channel plate 12 and substrate 22 allows one or both of these elements to be reused if desired.

Referring now to FIG. 6, in an alternative embodiment to that shown in FIG. 1, the height of the staging reservoir 16 and a collecting reservoir 18 may be increased and ports 24 and 27 provided through the channel plate 12 opposite the substrate 22. Upon initially filling staging reservoir 16 with carrier liquid 26 and polymeric molecules 36, a pressure head 52 is created being the difference in liquid height in staging reservoir 16 and a collecting reservoir 18. The small size of the micro-channel 14 limits flow from the staging reservoir 16 to the collecting reservoir 18 under normal gravitational acceleration after limited capillary flow.

Referring now to FIG. 8, the substrate 22 of the embodiment of FIG. 6 may be attached to a weighted carrier 54 that fits within the cup 56 of a standard swing bucket centrifuge 58 with the channel plate 12 supported to be level with the top of the cup 56 and the staging reservoir 16 and collecting reservoir 18 extending upward therefrom. The weighted carrier 54 is constructed so that the combination of the channel plate 12, the substrate 22, and the weighted carrier 54, when in position in the cup 56, have a center of mass 57 below the pivot 55 about which the cup is free to rotate.

When the centrifuge is started, as shown in FIG. 9, rotation 60 of the cups 56 swings them outward under the influence of a radial centripetal acceleration 62 acting on the center of mass 57. The acceleration promotes a downward force 64 shown in FIG. 6 on the carrier liquid 26 sufficient to cause the desired laminar flow through the micro-channel 14. By sizing the aperture of the micro-channel 14, and controlling the initial pressure head 52, the desired flow rate may be achieved.

Referring to FIGS. 6 and 7, a single channel plate 12 may incorporate multiple staging reservoirs 16, collecting reservoirs 18 and intervening micro-channels 14. As the pressure head 52 drops with flow through the micro-channel 14, the flow rate through the micro-channel 14 will also decrease. Control of this rate of decrease can be obtained by adjusting the relative diameter or cross-sectional area of staging reservoir 16 compared to collecting reservoir 18. For example, by making the collecting reservoirs 18 of bigger diameter than the staging reservoirs 16, the pressure head 52 decreases more slowly. By making the diameter of the reservoirs 16 and 18 large with respect to the flow rate or concentrating the polymeric molecules in the bottom of the staging reservoir 16, the molecules will pass through the micro-channel 14 only during the initial flow period providing more constant flow and transit time of the polymeric molecules 36 through the micro-channel 14.

Referring now to FIG. 10, in an alternative embodiment, the micro-channel 14 may be given a varying cross-sectional area so that for a given net flow rate 65 a series of different flow velocities V1 through V3 will be created at different locations along the micro-channel 14. It is believed that these varying flow velocities may effect a spatial separation of polymeric molecules 36 according to their length. This length sorting may be desirable to separate shorter polymeric molecules 36 from overlapping with longer polymeric molecules or for analytic separation of polymeric molecules 36 by length such as currently is done with electrophoresis.

Referring now to FIG. 11, the present invention may be incorporated as part of an optical mapping system. At a first step 70 of such a system, a solution, typically of water and polymeric molecules, for example, DNA, is prepared by techniques well known in the art. The polymeric molecules 36 may be treated with a condensing agent such as spermine causing them to coil, thereby reducing their damage during transfer to the apparatus 10 described above.

At step 72, the water (which will act as the carrier liquid 26) and polymeric molecules 36 are inserted into the staging reservoir 16. In the staging reservoir 16 they may be treated, for example, with a saline solution to decondense the molecules over a period, loosening their spermine-induced coiling. Once decondensed, the carrier fluid 26 and polymeric molecules 36 flow through the micro-channel 14 driven by a pump, centrifuge, or other method. During the flow, polymeric molecules 36 attach to the substrate 22 in straightened configuration.

Additional treatment of the fixed polymeric molecules 36 may be performed, as indicated by process block 74, by a variety of methods known in the art including but not limited to tagging with fluorescent materials or cutting by restriction enzymes. This step may include staining the polymeric molecules 36 with a fluorescent dye to provide accurate measurement of segments of the polymeric molecules 36.

These treatments may be performed either by passing additional liquids through the micro-channels 14 or by peeling back the channel plate 12 to allow direct access to the polymeric molecules 36 fixed to the substrate 22.

At process block 76, optical mapping of the fixed and treated polymeric molecules 36 may be performed either through the transparent optical mapping substrate 22 or by removing channel plate 12. After optical mapping, the fixed polymeric molecules 36 may be stored.

The laminar fluid flow used in the present invention, in contrast to radial or other capillary fluid flows is believed to reduce the number of overlapping molecules. The controlled laminar flow may also provide more consistent elongation or stretching of the polymeric molecules 36.

It is specifically intended that the present invention not be limited to the embodiments and illustrations contained herein, but include modified forms of those embodiments including portions of the embodiments and combinations of elements of different embodiments as come within the scope of the following claims.

We claim:

1. A method of straightening and fixing polymeric molecules having first and second ends, the method comprising the steps of:
   (a) putting the polymeric molecules in a carrier liquid;
   (b) passing the polymeric molecules and carrier liquid through a micro-channel having a first wall electrostatically attractive to the polymeric molecule to promote a laminar flow of carrier liquid in the micro-channel that straightens the polymeric molecule over its length until at least the first and second ends of the molecule attach to the first wall; and
   (c) detaching the first wall from the micro-channel.

2. The method of claim 1 further including the step of (d) applying restricting enzymes to the straightened polymeric molecule attached to the first wall.

3. The method of claim 1 further including the step of (d) optically inspecting the straightened polymeric molecule attached to the first wall.

4. The method of claim 1 wherein the polymeric molecules are treated with a condensation agent to collapse the polymeric molecules into shear resistant balls and wherein step (a) includes the step of placing the polymeric molecules and carrier liquid into a reservoir attached to the micro-channel and decondensing the polymeric molecules in the reservoir prior to step (b).

5. The method of claim 1 further including the step of treating at least one wall of the micro-channel to have a positive surface charge of predetermined density.

* * * * *